United States Patent
Neumann

(10) Patent No.: US 11,289,206 B2
(45) Date of Patent: Mar. 29, 2022

(54) ARTIFICIAL INTELLIGENCE METHODS AND SYSTEMS FOR CONSTITUTIONAL ANALYSIS USING OBJECTIVE FUNCTIONS

(71) Applicant: KPN Innovations, LLC, Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 16/890,686

(22) Filed: Jun. 2, 2020

(65) Prior Publication Data
US 2021/0375466 A1    Dec. 2, 2021

(51) Int. Cl.
*G16H 50/70*    (2018.01)
*G16H 50/30*    (2018.01)
(Continued)

(52) U.S. Cl.
CPC .......... *G16H 50/30* (2018.01); *G06K 9/6256* (2013.01); *G06N 20/00* (2019.01); *G16H 10/40* (2018.01)

(58) Field of Classification Search
CPC ... G16H 50/30; G16H 50/70; G06Q 50/22–24
See application file for complete search history.

(56) References Cited

U.S. PATENT DOCUMENTS 8,271,415 B2    9/2012    Iliff
8,370,070 B2    2/2013    Fernandez
(Continued)

FOREIGN PATENT DOCUMENTS

WO    WO-2006026383 A2 *    3/2006    ............. G16H 50/20
WO    2008058399    5/2008
(Continued)

OTHER PUBLICATIONS

"Forecasting life expectancy, years of life lost, and all-cause and cause-specific mortality for 250 causes of death: reference and alternative scenarios for 2016-40 for 195 countries and territories"; Foreman et al.; Global Health Metrics; Oct. 16, 2018 (Year: 2018).*

(Continued)

*Primary Examiner* — John A Pauls
(74) *Attorney, Agent, or Firm* — Caldwell Intellectual Property Law; Keegan Caldwell; Katherine Rubino

(57) ABSTRACT

A system for constitutional analysis using objective functions includes a computing device configured to generate a ranked list of diseases, by determining a plurality of disease impact score vectors for plurality of diseases, and generating and optimizing a first objective function of the impact score vectors, to receive, from a user, a plurality of user physiological history data, to identify, as a function of a disease state classifier, a plurality of disease states associated with the plurality of user physiological history data, to match at least a disease state of the plurality of disease states to the ranked list of diseases, and to generate a curative habitual pattern to alleviate the at least a disease state by combining intervention elements to form a curative habitual pattern candidates, calculating a curative impact score of each curative habitual pattern candidate, and selecting the curative habitual pattern using the curative impact score.

20 Claims, 4 Drawing Sheets

(51) Int. Cl.
  *G06N 20/00* (2019.01)
  *G06K 9/62* (2022.01)
  *G16H 10/40* (2018.01)

(56) References Cited

U.S. PATENT DOCUMENTS

| | | | |
|---|---|---|---|
| 8,532,938 | B2 | 9/2013 | Jung et al. |
| 8,697,370 | B2 | 4/2014 | Kas et al. |
| 8,762,167 | B2 | 6/2014 | Blander et al. |
| 9,120,852 | B2 | 9/2015 | Jouhanneaud |
| 9,207,242 | B2 | 12/2015 | Luk et al. |
| 10,460,074 | B2 * | 10/2019 | Tekumalla ............ G16H 50/30 |
| 2001/0051764 | A1 * | 12/2001 | Bardy .................. A61B 5/0031 600/300 |
| 2004/0122787 | A1 | 6/2004 | Avinash et al. |
| 2010/0070455 | A1 * | 3/2010 | Halperin ............... G16B 20/00 706/54 |
| 2010/0267052 | A1 | 10/2010 | Gelber et al. |
| 2010/0292545 | A1 * | 11/2010 | Berka ................... A61B 5/163 600/301 |
| 2011/0230733 | A1 | 9/2011 | Al-Ali |
| 2012/0016690 | A1 * | 1/2012 | Ramarajan ............ G16H 70/20 705/2 |
| 2014/0249790 | A1 * | 9/2014 | Spilker ............. G06K 9/00335 703/11 |
| 2014/0310019 | A1 | 10/2014 | Blander et al. |
| 2015/0079033 | A1 | 3/2015 | Shuber et al. |
| 2015/0252436 | A1 | 9/2015 | Samant et al. |
| 2016/0068916 | A1 | 3/2016 | Nekarda et al. |
| 2016/0367188 | A1 | 12/2016 | Malik et al. |
| 2017/0169163 | A1 * | 6/2017 | Shomron ................ C12Q 1/68 |
| 2018/0032698 | A1 | 2/2018 | Lau et al. |
| 2018/0106807 | A1 | 4/2018 | Redston |
| 2018/0306804 | A1 | 10/2018 | Micallef et al. |
| 2019/0025333 | A1 | 1/2019 | Zhang et al. |
| 2019/0074080 | A1 | 3/2019 | Appelbaum et al. |
| 2019/0078142 | A1 | 3/2019 | Apte et al. |
| 2019/0087536 | A1 | 3/2019 | Apte et al. |
| 2020/0303075 | A1 * | 9/2020 | Krishna ................ G16H 50/30 |

FOREIGN PATENT DOCUMENTS

| | | |
|---|---|---|
| WO | 1904006347 | 1/2014 |
| WO | 2014071455 | 5/2014 |
| WO | 2015085368 | 6/2015 |
| WO | 2017044885 | 3/2017 |
| WO | 2017044902 | 3/2017 |
| WO | 2018020239 | 2/2018 |

OTHER PUBLICATIONS

"Mixed-Integer Linear Programming Algorithms"; Math Works; Feb. 2, 2018 (Year: 2018).*

MagMAX CORE Nucleic Acid Purification Kit, Flyer, 2019, ThermoFisher Scientific.

* cited by examiner

ARTIFICIAL INTELLIGENCE METHODS AND SYSTEMS FOR CONSTITUTIONAL ANALYSIS USING OBJECTIVE FUNCTIONS

FIELD OF THE INVENTION

The present invention generally relates to the field of objective function optimization. In particular, the present invention is directed to methods and systems for constitutional analysis using objective functions.

BACKGROUND

Artificial intelligence methods are increasingly valuable for analysis of patterns in large quantities of data. However, where the data is large and varied enough, tradeoffs between sophistication and efficiency can become untenable.

SUMMARY OF THE DISCLOSURE

In an aspect, a system for constitutional analysis using objective functions includes a computing device configured to generate a ranked list of diseases, wherein generating further comprises determining a plurality of disease impact score vectors associated with a plurality of diseases, wherein each disease impact score vector includes at least a disease impact score, generating a first objective function of the impact score vectors, and ranking the diseases according to optimization of the first objective function. Computing device is configured to receive, from a user, a plurality of user physiological history data. Computing device is configured to identify, as a function of a disease state classifier, a plurality of disease states associated with the plurality of user physiological history data. Computing device is configured to match at least a disease state of the plurality of disease states to the ranked list of diseases. Computing device is configured to generate a curative habitual pattern to alleviate the at least a disease state, wherein generating further includes forming a query using the at least a disease state, retrieving, from an intervention listing datastore, a plurality of intervention elements as a function of the query, combining the plurality of intervention elements to form a plurality of curative habitual pattern candidates, calculating a curative impact score of each curative habitual pattern candidate of the plurality of curative habitual pattern candidates, and selecting the curative habitual pattern from the plurality of curative habitual pattern candidates as a function of the curative impact score.

In another aspect a method of constitutional analysis using objective functions includes generating, by a computing device, a ranked list of diseases, wherein generating further includes determining a plurality of disease impact score vectors associated with a plurality of diseases, wherein each disease impact score vector includes at least a disease impact score, generating a first objective function of the impact score vectors, and ranking the diseases according to optimization of the first objective function. The method includes receiving, by the computing device and from a user, a plurality of user physiological history data. The method includes identifying, by the computing device and as a function of a disease state classifier, a plurality of disease states associated with the plurality of user physiological history data. The method includes matching, by the computing device, at least a disease state of the plurality of disease states to the ranked list of diseases. The method includes generating, by the computing device, a curative habitual pattern to alleviate the at least a disease state, wherein generating further includes forming a query using the at least a disease state, retrieving, from an intervention listing datastore, a plurality of intervention elements as a function of the query, combining the plurality of intervention elements to form a plurality of curative habitual pattern candidates, calculating a curative impact score of each curative habitual pattern candidate of the plurality of curative habitual pattern candidates, and selecting the curative habitual pattern from the plurality of curative habitual pattern candidates as a function of the curative impact score.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, embodiments described herein improve speed and accuracy in analysis of constitutional and/or physiological data by selecting a subset of maximally impactful conditions and restricting analysis to outputs pertaining to the subset. Objective functions may be used to select the subset based on numerical scoring derived from machine-learning processes. Further classification of physiological data to conditions may enable detection and alleviation thereof in users.

Figure 1:
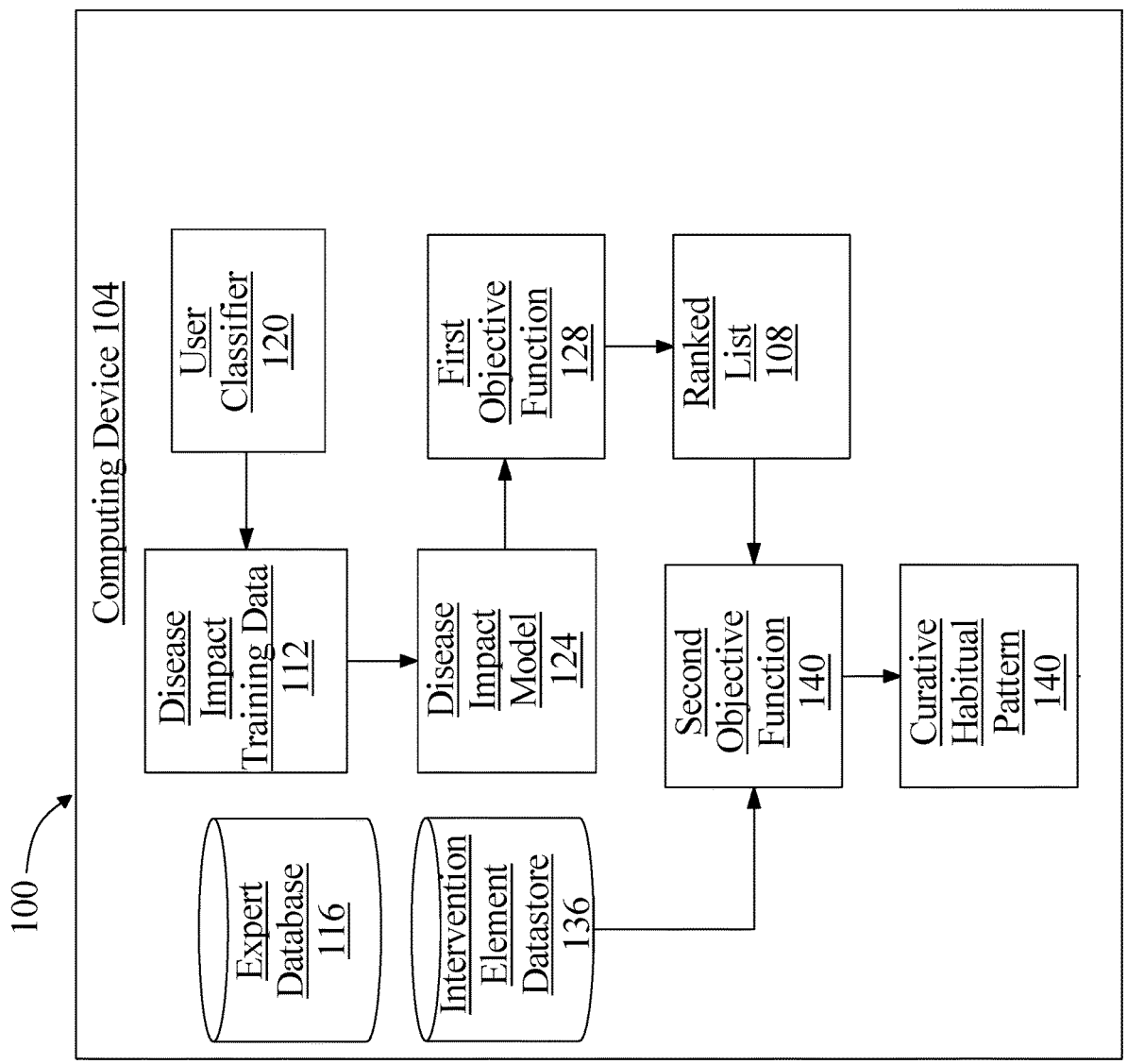
FIG. 1 is a block diagram illustrating an exemplary embodiment of a system for constitutional analysis using objective functions.

Referring now to FIG. 1, an exemplary embodiment of a system 100 for constitutional analysis using objective functions is illustrated. System includes a computing device 104. Computing device 104 may include any computing device 104 as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing device 104 operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device 104.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to generate a ranked list 108 of diseases. In an embodiment, computing device 104 may generate ranked list 108 by determining a plurality of disease impact score vectors associated with a plurality of diseases. Each disease impact score vector includes at least a disease impact score. A "disease impact score," as used in this disclosure, is a score measuring an overall impact of a disease in reduction of longevity and quality of life. For instance, and without limitation, a disease impact score may measure a likely reduction in lifespan due to a corresponding disease; for instance, atherosclerosis may remove some average number of years from a person's life expectancy, while a certain type of cancer may remove a different average number of years; a larger reduction in lifespan may be given a higher impact score. An additional example of an impact score may be a score assessing a degree of disability, as measured in years of disability, severity of disability, and/or progression of disability, for instance to assess a degree to which the disease makes full enjoyment of life difficult or impossible. For instance, and without limitation, a condition such as without limitation osteoarthritis, rheumatoid arthritis, congestive heart failure, multiple sclerosis, or some cancers may be degenerative, and may gradually increase debility leading to a number of years of extreme disability; such a condition may receive a higher score than a condition that does not cause a lengthy period of severe disability. A further exemplary impact score may be based on an age of onset of a disease, where an earlier age of onset may be associated with a higher impact score. An additional exemplary impact score may relate to an average age at death. Another exemplary impact score may describe a frequency of a condition and/or deaths therefrom within a population; for instance, heart disease, chronic lower respiratory illnesses, cerebrovascular disease, and Alzheimer's disease may all receive high impact scores related to frequency. A further exemplary impact score may measure a degree to susceptibility of improvement through curative habitual patterns as described below, such as improvements to diet, nutrition, fitness, emotional health, or the like, where a disease more easily prevented and/or alleviated through such interventions, such as type II diabetes or heart disease, may have a higher score than a disease such as Huntington's disease, which may not be materially affected by such interventions. Persons skilled in the art, upon reviewing the entirety of this disclosure, will be aware of various alternative or additional impact scores that may be used consistently with this disclosure.

With continued reference to FIG. 1, a "vector" as defined in this disclosure is a data structure that represents one or more quantitative values and/or measures such as disease impact scores. A vector may be represented as an n-tuple of values, where n is at least two values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes.

Still referring to FIG. 1, computing device 104 may determine a plurality of impact score vectors and/or disease impact scores by various methods, including receiving statistics reported from health reporting agencies and/or devices operated thereby, for instance describing age of onset and/or age of death from various diseases, statistical analysis of data describing such diseases, or the like. Receiving data describing such diseases may include receiving disease impact training data 112. "Training data," as used herein, is data containing correlations that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, training data may include one or more elements that are not categorized; that is, training data may not be formatted or contain descriptors for some elements of data. Machine-learning processes and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below. Training data used by computing device 104 may correlate any input data as described in this disclosure to any output data as described in this disclosure.

As a non-limiting example, and with continued reference to FIG. 1, disease impact training data 112 including a plurality of entries correlating diseases of the plurality of diseases with disease impact scores, where correlation with disease impact scores may include correlation with data convertible to impact scores; for instance, a number of years lost, and/or a set of parameters such as life expectancy and age of death from a disease that may be mathematically equivalent, may be treated as convertible to an impact score measuring an expected and/or average loss of lifespan.

Still referring to FIG. 1, disease impact training data 112 may be received and/or collated from various sources. For instance, a source of disease impact training data 112 may include one or more reporting agencies such as the Center for Disease Control (CDC), National Institute of Health (NIH) or the like. Alternatively or additionally, disease impact training data 112 may be received in the form of one or more expert inputs. Expert inputs may be received directly and/or stored in an expert database 116. Expert database 116 may be implemented, without limitation, as a relational expert database 116, a key-value retrieval expert database 116 such as a NOSQL expert database 116, or any other format or structure for use as an expert database 116 that a person skilled in the art would recognize as suitable upon review of the entirety of this disclosure. Expert database 116 may alternatively or additionally be implemented using a distributed data storage protocol and/or data structure, such as a distributed hash table or the like. Expert database 116 may include a plurality of data entries and/or records as described above. Data entries in an expert database 116 may be flagged with or linked to one or more additional elements of information, which may be reflected in data entry cells and/or in linked tables such as tables related by one or more indices in a relational expert database 116. Persons skilled in the art, upon reviewing the entirety of this disclosure, will be aware of various ways in which data entries in an expert database 116 may store, retrieve, organize, and/or reflect data and/or records as used herein, as well as categories and/or populations of data consistently with this disclosure.

Figure 2:
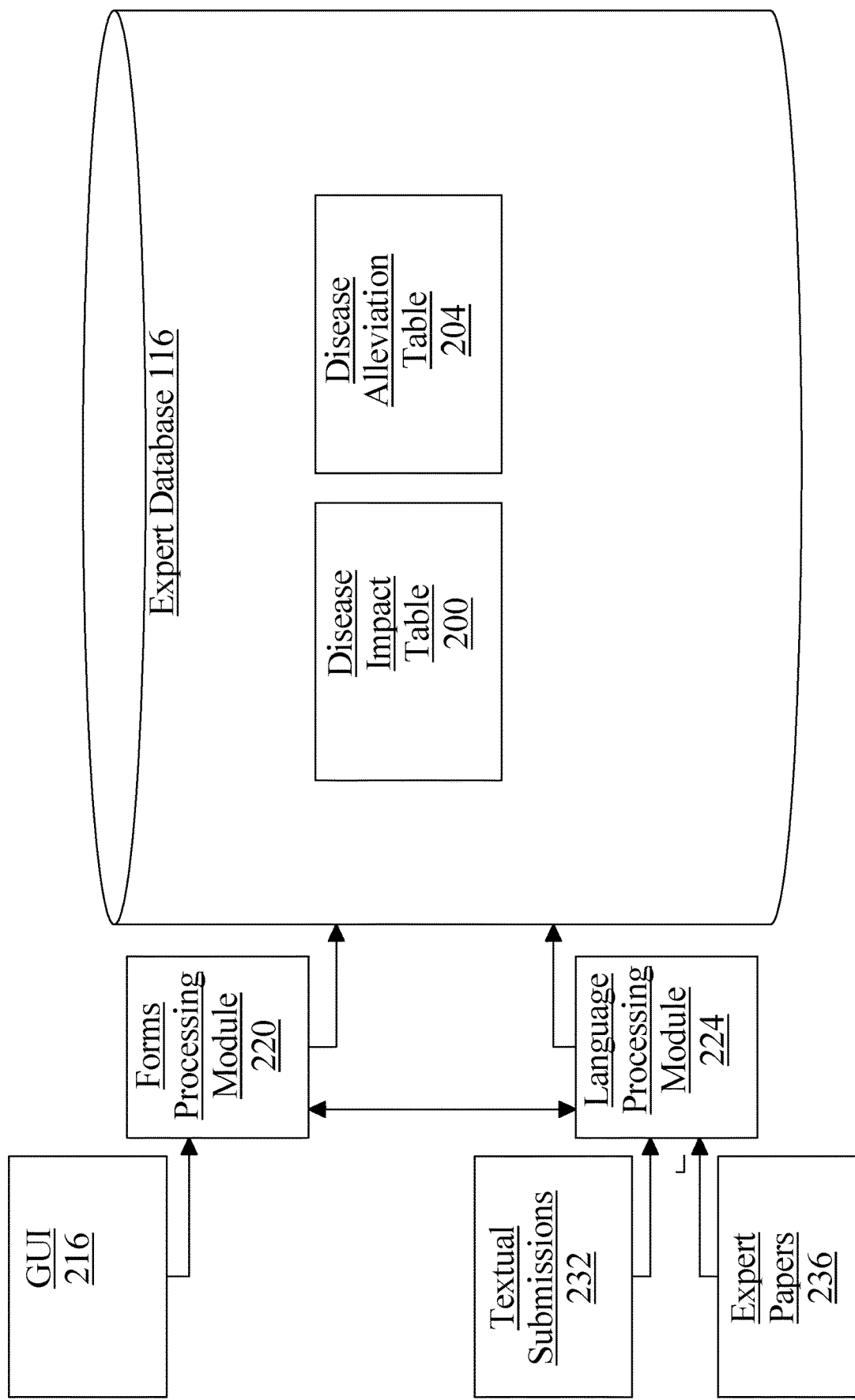
FIG. 2 is a block diagram illustrating an exemplary embodiment of an expert database.

Referring now to FIG. 2, an exemplary embodiment of an expert database 116 is illustrated. Expert database 116 may, as a non-limiting example, organize data stored in the expert database 116 according to one or more database tables. One or more database tables may be linked to one another by, for instance, common column values. For instance, a common column between two tables of expert database 116 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in expert database 116 may include, as a non-limiting example, a disease impact table 200. Disease impact table 200 may list disease impact scores and/or quantities suitable for calculation thereof, as reported by experts. For instance, and without limitation, columns listed in disease impact table may correspond to net effect on life expectancy, degree of disability, age of onset, frequency within population, and/or other elements suitable for use as an impact score. One or more database tables in expert database 116 may include, as a non-limiting example, a disease alleviation table 204. Disease alleviation table 204 may contain entries associating each disease of a plurality of disease with curative habitual patterns, as defined below, identified by experts as affecting impact of a subject disease, and/or a degree of reduction in any impact score, such as a probability of prevention, reduction of lifespan impact (i.e. years of lifespan regained by use of curative habitual patterns), reduction of disability, or the like.

In an embodiment, and still referring to FIG. 2, a forms processing module 208 may sort data entered in a submission via a graphical user interface 212 receiving expert submissions by, for instance, sorting data from entries in the graphical user interface 212 to related categories of data; for instance, data entered in an entry relating in the graphical user interface 212 to disease impacts may be sorted into variables and/or data structures for impact score data, which may be provided to disease impact 200, while data entered in an entry relating to alleviation of disease using curative habitual patterns may be sorted into variables and/or data structures for the storage of such data, such as disease alleviation table 204. Where data is chosen by an expert from pre-selected entries such as drop-down lists, data may be stored directly; where data is entered in textual form, a language processing module may be used to map data to an appropriate existing label, for instance using a vector similarity test or other synonym-sensitive language processing test to map data to existing labels and/or categories. Similarly, data from an expert textual submissions 216, such as accomplished by filling out a paper or PDF form and/or submitting narrative information, may likewise be processed using language processing module, which may be implemented, without limitation as described in U.S. Nonprovisional Application Ser. No. 16/372,512, filed on Apr. 2, 2019, and entitled METHODS AND SYSTEMS FOR UTILIZING DIAGNOSTICS FOR INFORMED VIBRANT CONSTITUTIONAL GUIDANCE, the entirety of which is incorporated herein by reference.

Data may be extracted from expert papers 224, which may include without limitation publications in medical and/or scientific journals, by language processing module 220 via any suitable process as described herein. Persons skilled in the art, upon reviewing the entirety of this disclosure, will be aware of various additional methods whereby novel terms may be separated from already-classified terms and/or synonyms therefore, as consistent with this disclosure.

In an embodiment, and referring again to FIG. 1, disease impact training data 112 may be limited to one or more categories of users and/or persons. For instance, and without limitation, one population of people defined by one or more demographic traits may be impacted differently by one disease than by another; as an example, certain cancers, such as prostate cancer, may be far more prevalent in men than in women, while some autoimmune conditions may be far more prevalent in women than in men. In addition to sex, further categories to which training data may be limited may include, without limitation, ethnicity, national origin, age, blood type, or the like. Training data may be limited to intersections and/or unions of such categories, so that for instance, training data may be limited for some purposes to Caucasian women above 40, or the like; some of the same elements training data may also be sorted separately to two or more categories in successive sorting processes, such that for instance data relating to a Caucasian woman or, set of Caucasian women, over 40 may also be sorted to a category of Caucasian people, people over 40, and/or women. Sorting of training data into categories may be performed using at least a user classifier 120. Categories may be listed in expert database 116 and/or received as expert submissions; for instance, experts and/or expert submissions may identify statistically useful categories for the purposes of impact score determination.

Further referring to FIG. 1, a "classifier," such as without limitation a user classifier 120, is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)+P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may train a disease impact model 124 as a function of the disease impact training data 112 and a machine-learning process and determine the plurality of impact score vectors as a function of the disease impact model 124. A "machine learning process," as used in this disclosure, is a process that automatedly uses a body of data known as "training data" and/or a "training set" to generate an process that will be performed by a computing device 104/module to produce outputs given data provided as inputs; this is in contrast to a non-machine learning software program where the commands to be executed are determined in advance by a user and written in a programming language.

With continued reference to FIG. 1, machine-learning process may include without limitation a regression process such as a linear regression process. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples.

Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 1, machine-learning process may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, models may be generated using alternative or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using training data.

Still referring to FIG., machine-learning process may include at least a supervised machine-learning algorithm. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include diseases, and/or labels identifying diseases, as described above as inputs, impact scores as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data. Persons skilled in the art, upon reviewing the entirety of this disclosure, will be aware of various possible variations of supervised machine learning algorithms that may be used to determine relation between inputs and outputs.

Further referring to FIG. 1, disease impact model 124 may output each impact score for each disease of plurality of diseases; each impact score may be calculated per disease. In an embodiment, disease treatment model may include a model per category of user category according to which trading data is sorted as described above, generating a plurality of category-specific disease impact models 124.

Still referring to FIG. 1, computing device 104 is configured to generate a first objective function 128 of the impact score vectors. An "objective function," as used in this disclosure, is a mathematical function used by a computing device 104 to score a quantitative element such as an impact score vector, which may include one impact score and/or a plurality of objective scores. In various embodiments a score of a particular impact scored vector may be based on a combination of one or more factors, including impact scores. Each impact score vector may be assigned a score based on predetermined variables. In some embodiments, the assigned scores may be weighted or unweighted. Computing device 104 may compute a score associated with each impact score vector and select impact score vectors to minimize and/or maximize the score, depending on whether an optimal result is represented, respectively, by a minimal and/or maximal score.

Continuing to refer to FIG. 1, computing device 104 is configured to produce ranked list 108 by ranking diseases according to optimization of first objective function 128. Objective function may be formulated as a linear objective function, which computing device 104 may solve using a linear program such as without limitation a mixed-integer program. A "linear program," as used in this disclosure, is a program that optimizes a linear objective function, given at least a constraint. For instance, a lifespan impact may be constrained to less than an actuarially predicted year of death minus age of onset, while an amount of years of lifespan recoverable using a curative habitual pattern, as described in further detail below, may be constrained to less than the lifespan impact. In various embodiments, system 100 may determine impact score vector that maximizes a total score subject to at least a constraint. A mathematical solver may be implemented to solve for the set disease impact vectors that maximizes scores; mathematical solver may implemented on computing device 104 and/or another device in system 100, and/or may be implemented on third-party solver. A higher score may, for instance, be given to a disease that has a high lifespan impact, an impact score indicating a high degree of disability caused by the disease, and a high impact score relating to susceptibility for improvement using curative habitual patterns.

With continued reference to FIG. 1, optimizing objective function may include minimizing a loss function, where a "loss function" is an expression an output of which an optimization algorithm minimizes to generate an optimal result. As a non-limiting example, computing device 104 may assign variables relating to a set of parameters, which may correspond to score components as described above, calculate an output of mathematical expression using the variables, and select a disease impact vector that produces an output having the lowest size, according to a given definition of "size," of the set of outputs representing each of plurality of candidate ingredient combinations; size may, for instance, included absolute value, numerical size, or the like. Selection of different loss functions may result in identification of different disease impact vectors as generating minimal outputs.

Still referring to FIG. 1, computing device 104 may rank diseases according to degree to which corresponding disease impact vectors optimize first objective function 128; this may result in a ranked list 108 in which higher-ranking diseases are more common, result in a greater average loss of life expectancy, result in a greater average degree and/or duration of disability, and/or are more susceptible to improvement through curative habitual patterns, than other entries on the list. Computing device 104 may be configured to eliminate from the ranked list 108 all but a number of top-ranking diseases on the list, where the number may be, without limitation 100, 300, or the like; alternatively or additionally, computing device 104 may compare an objective function output of each of plurality of devices to a preconfigured threshold number and/or ranking, and eliminate from ranked list 108 all disease having associated objective function outputs failing threshold by being, depending on the form of the threshold comparison and objective function, greater than or less than the threshold. Addressing diseases on ranked list 108, using curative habitual patterns, in descending order of ranking may produce a maximal likely increase in lifespan and/or years of minimal disability for a user.

Still referring to FIG. 1, computing device 104 is configured to receive a plurality of user physiological history data from a user. "User physiological history data," as used in this disclosure, is any medical and/or health history data pertaining to a user. An element of user physiological history data may include a user reported an element of user physiological history data. A user reported element of user physiological history data may include any medical data pertaining to a user, supplied by a user. For example, a user reported element of user physiological history data may include any previous health history, health records, diagnosis, medications, treatments, major surgeries, complications, and the like that the user may be suffering from. For example, a user reported an element of user physiological history data may include an anaphylactic reaction to all tree nuts that the user was diagnosed with as a young child. In yet another non-limiting example, a user reported element of user physiological history data may describe a previous diagnosis such as endometriosis that the user was diagnosed with three years back, and treatments that the user engages in to manage her endometriosis, including supplementation with fish oil and following a gluten free diet. In yet another non-limiting example, a user may provide one or more elements of health history information, such as when a user may select how much of a user's medical records the user seeks to share with computing device 104. For example, a user may prefer to share only the user's hospitalization records and not the user's current medication list. In yet another non-limiting example, a user may seek to share as many records as are available for the user, such as the user's entire vaccination history. In yet another non-limiting example, a user may share health history information that is available to the user, such as when records may become lost or misplaced. An element of user physiological history data may include an amount of information or certain records based on a user's entire medical record that the user seeks to share and allow system 100 and/or a computing device 104 to have access to. For example, a user may prefer to share only the user's hospitalization records and not the user's current medication list. In yet another non-limiting example, a user may seek to share as many records as are available for the user, such as the user's entire health history. In yet another non-limiting example, a user may not wish to share any information pertaining to a user's health history. In yet another non-limiting example, a user may be unable to share any information pertaining to a user's health history, because the user may be adopted and may not have access to health records, or the user is unable to locate any health records for the user and the like.

With continued reference to FIG. 1, an element of user physiological history data may include a user reported self-assessment. A "self-assessment" as used in this disclosure, is any questionnaire that may prompt and/or ask a user for any element of user health history. For instance and without limitation, a self-assessment may seek to obtain information including demographic information such as a user's full legal name, sex, date of birth, marital status, date of last physical exam and the like. A self-assessment may seek to obtain information regarding a user's childhood illness such as if the user suffered from measles, mumps, rubella, chickenpox, rheumatic fever, polio, and the like. A self-assessment may seek to obtain any vaccination information and dates a user received vaccinations such as tetanus, hepatitis, influenza, pneumonia, chickenpox, measles mumps and rubella (MMR), and the like. A self-assessment may seek to obtain any medical problems that other doctors and/or medical professionals may have diagnosed. A self-assessment may seek to obtain any information about surgeries or hospitalizations the user experienced. A self-assessment may seek to obtain information about previously prescribed drugs, over-the-counter drugs, supplements, vitamins, and/or inhalers the user was prescribed. A self-assessment may seek to obtain information regarding a user's health habits such as exercise preferences, nutrition and diet that a user follows, caffeine consumption, alcohol consumption, tobacco use, recreational drug use, sexual health, personal safety, family health history, mental health, other problems, other remarks, information pertaining to women only, information pertaining to men only and the like.

Alternatively or additionally, and further referring to FIG. 1, plurality of user physiological history data may include biological extraction data. Biological extraction data may include any data used as a biological extraction as described in U.S. Nonprovisional application Ser. No. 16/502,835, filed on Jul. 3, 2019, and entitled "METHODS AND SYSTEMS FOR ACHIEVING VIBRANT CONSTITUTION BASED ON USER INPUTS," the entirety of which is incorporated herein by reference.

Still referring to FIG. 1, computing device 104 may identify a plurality of disease states associated with the plurality of user physiological history data as a function of a disease state classifier 132. A "disease state," as used in this disclosure, is a current diagnosis and/or prediction of a future diagnosis of a disease as described above; for instance a disease state may include a current diagnosis of diabetes, a current classification as "prediabetic," and/or an identification that user may be at risk for a diagnosis of diabetes in the future owing to body mass index, family history, diet, genetic markers, or the like. Disease state classifier 132 may be implemented, without limitation, using any classification process suitable for implementation of user classifier 120 as described above. Training data for disease state classifier 132 may include a plurality of entries including user physiological history data and labels of disease states. Training data may be received, without limitation, from expert submissions and/or expert database 116, from case histories, and/or records of past data processed by system 100 and/or systems and/or devices in communication therewith; for instance a user that submitted user physiological history data, as described above to system may have been concurrently and/or subsequently recorded as having suffered from one or more diseases, which data may be used to generate one or more training data entries for training disease state classifier 132. In an embodiment, user may be classified to one or more categories of users as described above, and training data for disease state classifier 132 may be limited to training data corresponding to the one or more categories of users. Computing device 104 and/or any other device may train disease state classifier 132 using training data.

With continued reference to FIG. 1, computing device 104 may be further configured to computing one or more elements of data predicting any impact score, as defined above for any disease state as applied to user; this may be performed using training data correlating elements of user physiological history data with impact score quantities, for instance based on expert inputs and/or data from an expert database 116 as described above, and/or using data records collected in iterations of methods described in this disclosure, related processes performed by system 100, and/or information entered by one or more users describing outcomes of one or more methods as described herein when practiced by users. Training data may be used to train a user impact score model using any machine-learning process as described above, to which computing device 104 may input user physiological data received from instant user to receive from the model user-specific impact scores. For instance, computing device 104 may further be configured to determine an age of onset of each disease state of plurality of disease states, where the age of onset is an actual and/or predicted age of onset of a disease state for the user. Computing device 104 may be further configured to determine a likelihood of each disease state of plurality of disease states; for instance, where a disease state is a possible or likely future disease user may suffer, computing device 104 may determine a probability that the user will actually suffer and/or is currently suffering from the disease; this may be performed using training data correlating elements of user physiological history data with probabilities of suffering disease states, for instance based on expert inputs and/or data from an expert database 116 as described above, and/or using data records collected in iterations of methods described in this disclosure, related processes performed by system 100, and/or information entered by one or more users describing outcomes of one or more methods as described herein when practiced by users. Training data may be used to train a disease state probability model using any machine-learning process as described above, to which computing device 104 may input user physiological data received from instant user to receive from the model user-specific impact scores. Probabilities of suffering a current and/or future disease, as well as other impact score data, may alternatively or additionally be determined as described in U.S. Nonprovisional application Ser. No. 16/502,835. In an embodiment, computing device 104 may weight ranked list 108 used for user as described above; weighting may include multiplying the likelihood of the disease state by an output of the first objective function 128 for a corresponding disease of the plurality of diseases. Ranked list 108 may be re-ranked according to weighting, prior to subsequent steps performed by computing device 104.

Further referring to FIG. 1, computing device 104 is configured to match at least a disease state of the plurality of disease states to the ranked list 108 of diseases. Matching may include comparing labels of disease states to labels of diseases on ranked list 108 of diseases; for instance, disease states and corresponding diseases may share identical labels. In an embodiment, computing device 104 may classify user to one or more categories of users and at least a ranked list 108 computed, as above, for the one or more categories may be used for matching. For instance, user may be classified to one or more categories of user as a function of user classifier 120, to which computing device 104 may input one or more elements of user data such as without limitation user demographic data and/or user physiological data as described above; where user is classified to more than one category in one or more user classifiers 120 as described above, a category may be selected as a most significant category, and a ranked list 108 associated therewith may be used. Alternatively or additionally, ranked lists 108 corresponding to a plurality of categories matching user may be averaged or otherwise aggregated, for instance by averaging and/or aggregating ranking for each disease on lists, to produce a user-specific ranked list 108.

Still referring to FIG. 1, computing device 104 is configured to generate a curative habitual pattern to alleviate the at least a disease state. A "curative habitual pattern," as used in this disclosure is a set of regularly applied fitness, nutrition, and/or dietary actions tending to improve, prevent, and/or alleviate one or more disease states. A curative habitual pattern may include, without limitation a curative nutritional pattern, which is a curative habitual pattern with regard to nutritional input. Curative nutritional pattern may include regular consumption, cessation of consumption, or consumption of particular quantities of food and/or supplements. Curative nutritional pattern may include regulation of calories or other aggregate measures of nutritional intake. Curative nutritional pattern may include regulations of particular nutrient quantities to be consumed. Curative nutritional pattern may include one or more schedules for fasting, for instance in patterns, schedules and/or plans that integrate food consumed, fasting, sleep, exercise, supplementation, current disease state, and the like for optimal fasting results. Curative habitual pattern may include a curative exercise pattern, which may include without limitation an exercise schedule and/or plan for improvement of health. Curative habitual pattern may include a pattern of meditation and/or spiritual practices, a pattern of therapy, a pattern of consultation with an advisor, therapist, family member, or the like, or any other pattern of behavioral habits that may act to improve, prevent, and/or alleviate one or more disease states.

Continuing to refer to FIG. 1, computing device 104 is configured to generate the curative habitual pattern by providing a plurality of curative habitual patterns; this may be accomplished, without limitation, by forming a query using the at least a disease state; query may include without limitation a label and/or plurality of labels for disease states. Computing device 104 may retrieve a plurality of intervention elements from an intervention listing datastore as a function of the query. An "intervention element," as used in this disclosure is a single habit that may be incorporated in a curative habitual pattern; for instance, a single dietary rule such as without limitation eating a certain number of servings of fruit per day, eating fewer than a certain number of grams of sugar per day, getting at least 20 minutes of cardiovascular exercise per day, or the like. Each intervention element may be represented by a plurality of impact scores associated with the intervention element, which may be listed in records in intervention database 136. Intervention database 136 may be implemented in any manner suitable for implementation of expert database 116 as described above.

Still referring to FIG. 1, impact scores associated with intervention elements, for instance as stored in intervention listing datastore, may be populated by expert submission received as described above, including without limitation records populated within disease alleviation table 204. Alternatively or additionally, population of impact scores in intervention listing datastore may be performed using training data correlating intervention elements and/or labels thereof with impact score quantities, for instance based on expert inputs and/or data from an expert database 116 as described above, such as without limitation from disease alleviation table 204, and/or using data records collected in iterations of methods described in this disclosure, related processes performed by system 100, and/or information entered by one or more users describing outcomes of one or more methods as described herein when practiced by users. Training data may be used to train an intervention impact score model using any machine-learning process as described above, to which computing device 104 may input user physiological data received from instant user to receive from the model impact scores corresponding to intervention elements. Intervention elements and/or impacts thereof may alternatively or additionally be identified as described in U.S. Nonprovisional application Ser. No. 16/502,835.

Still referring to FIG. 1, computing device 104 may combine the plurality of intervention elements to form a plurality of curative habitual pattern candidates. Computing device 104 may combine intervention elements into curative habitual pattern candidates by aggregating vectors of impact scores of intervention elements; aggregation may be performed using any suitable method for aggregation, including component-wise addition followed by normalization, component-wise calculation of arithmetic means, or the like. Persons skilled in the art, upon reviewing the entirety of this disclosure, will be aware of various ways in which multiple intervention elements may be combined to create a vector associated with a curative habitual pattern candidate. Computing device 104 may implement one or more rules preventing combination of mutually exclusive and/or overlapping intervention elements. For instance, and without limitation, an intervention element for an exercise program may be identified with an exercise program identifier and may be prevented from combination with another element having the same flag; other categories of intervention element may similarly be flagged and prevented from combination, such that nutritional interventions, for instance, may be treated as mutually exclusive. Valid combinations within categories may be populated in intervention listing datastore by processes as described above, for instance by inclusion in training data, intervention listing datastore and/or machine-learning model inputs under labels identifying such combinations.

Further referring to FIG. 1, computing device 104 may calculate a curative impact score of each curative habitual pattern candidate of the plurality of curative habitual pattern candidates. A "curative impact score," as used in this disclosure, is a numerical quantity indicating a degree to which aggregated intervention element scores making up a vector thereof corresponding to curative habitual pattern candidate maximizes overall improvement to lifespan and quality of life analogously to reductions thereof represented by outputs of first objective function 128. Calculating curative impact score may include generating a second objective function 140 of the plurality of curative habitual pattern candidates; second objective function 140 may be implemented in any manner suitable for implementation of first objective function 128 as described above. Generating second objective function 140 may include receiving curative training data. Curative training data may include a plurality of entries, each entry correlating a curative habitual pattern candidate with at least a curative impact element. Computing device 104 may train a curative machine-learning model as a function of the curative training data and a machine-learning process, wherein the curative machine-learning model inputs curative habitual patter candidates and outputs curative impact vectors, each curative impact vector comprising at least a curative impact element; this may be performed as described above for calculation of intervention element impact scores. Objective function may be a function of curative impact vectors. In other words, computing device 104 may generate second objective function 140 as an objective function of the curative impact vectors. Second objective function 140 may be formulated, without limitation as a linear and/or mixed-integer objective function, and/or as a loss function; constraints for optimization may be implemented as described above for constraints for first objective function 128. Computing device 104 may optimize second objective function 140; this may be implemented in any manner suitable for optimization of first objective function 128 as described above.

Still referring to FIG. 1, computing device 104 is further configured to select curative habitual pattern from plurality of curative habitual pattern candidates as a function of curative impact score. For instance, and without limitation, computing device 104 may rank curative habitual pattern candidates according to curative impact scores and select a highest ranking curative habitual pattern candidate. A user may enter an instruction indicating that user is not going to perform selected curative habitual pattern; computing device 104 may display to user a next highest ranking curative habitual pattern, which may be iteratively repeated until user enters an instruction indicating that user will use a selected curative habitual pattern 144. As a further example, computing device 104 may present curative habitual patterns in rank order to user; computing device 104 may receive user selection of a user curative habitual pattern candidate and select curative habitual pattern as a function of the user selection.

Figure 3:
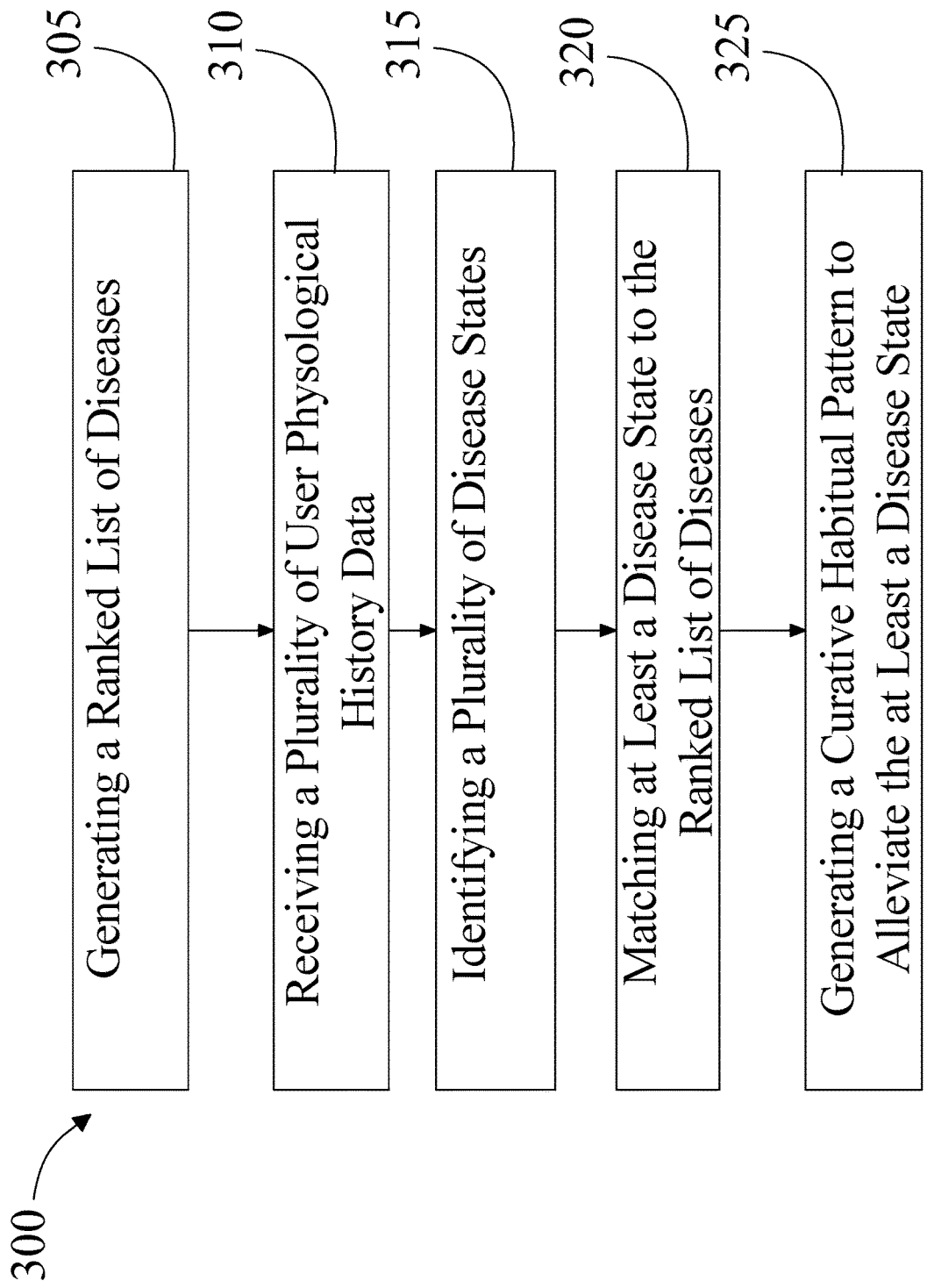
FIG. 3 is a flow diagram illustrating a method of constitutional analysis using objective functions.

Referring now to FIG. 3, an exemplary embodiment of a method 300 of constitutional analysis using first objective functions 128, is illustrated. At step 305, a computing device 104 generates a ranked list 108 of diseases; this may be implemented, without limitation, as described above in reference to FIGS. 1-2. Generating may include determining a plurality of disease impact score vectors associated with a plurality of diseases, each disease impact score vector including at least a disease impact score. Determining plurality of impact score vectors may include receiving disease impact training data 112, which the disease impact training data 112 including a plurality of entries correlating diseases of the plurality of diseases with disease impact scores, training a disease impact model 124 as a function of the disease impact training data 112 and a machine-learning process, and determining the plurality of impact score vectors as a function of the disease impact model 124. Computing device 104 generates a first objective function 128 of the impact score vectors; this may be implemented, without limitation, as described above in reference to FIGS. 1-2. First objective function 128 may include a linear objective function. First objective function 128 may include a mixed integer objective function. Computing device 104 ranks the diseases according to optimization of the first objective function 128; this may be implemented, without limitation, as described above in reference to FIGS. 1-2. Plurality of user physiological history data may include user-reported data. Plurality of user physiological history data may include biological extraction data.

At step 310, computing device 104 receives, from a user, a plurality of user physiological history data; this may be implemented, without limitation, as described above in reference to FIGS. 1-2. At step 315, computing device 104 identifies, as a function of a disease state classifier 132, a plurality of disease states associated with plurality of user physiological history data; this may be implemented, without limitation, as described above in reference to FIGS. 1-2. Identifying plurality of disease states may include determining an age of onset of each disease state of the plurality of disease states. Identifying plurality of disease states may include determining a likelihood of each disease state of the plurality of disease states. Computing device 104 may weight each element of the ranked list 108, wherein weighting further includes multiplying a likelihood of a disease state corresponding to an entry in the ranked list 108 by an output of first objective function 128 for a corresponding disease of plurality of diseases.

At step 320, and with continued reference to FIG. 3, computing device 104 matches at least a disease state of plurality of disease states to ranked list 108 of diseases; this may be implemented, without limitation, as described above in reference to FIGS. 1-2. At step 325, computing device 104 generates a curative habitual pattern to alleviate the at least a disease state; this may be implemented, without limitation, as described above in reference to FIGS. 1-2. Generating may include forming a query using the at least a disease state, retrieving, from an intervention listing datastore, a plurality of intervention elements as a function of the query, combining the plurality of intervention elements to form a plurality of curative habitual pattern candidates, calculating a curative impact score of each curative habitual pattern candidate of the plurality of curative habitual pattern candidates, and selecting the curative habitual pattern from the plurality of curative habitual pattern candidates as a function of the curative impact score. Calculating curative impact score may include generating a second objective function 140 of the plurality of curative habitual pattern candidate and optimizing the second objective function 140. Generating second objective function 140 may include receiving curative training data, the curative training data including a plurality of entries, each entry correlating a curative habitual pattern candidate with at least a curative impact element, training a curative machine-learning model as a function of the curative training data and a machine-learning process, wherein the curative machine-learning model inputs curative habitual patter candidates and outputs curative impact vectors, each curative impact vector comprising at least a curative impact element, and generating the second objective function 140 as an objective function of the curative impact vectors.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 4:
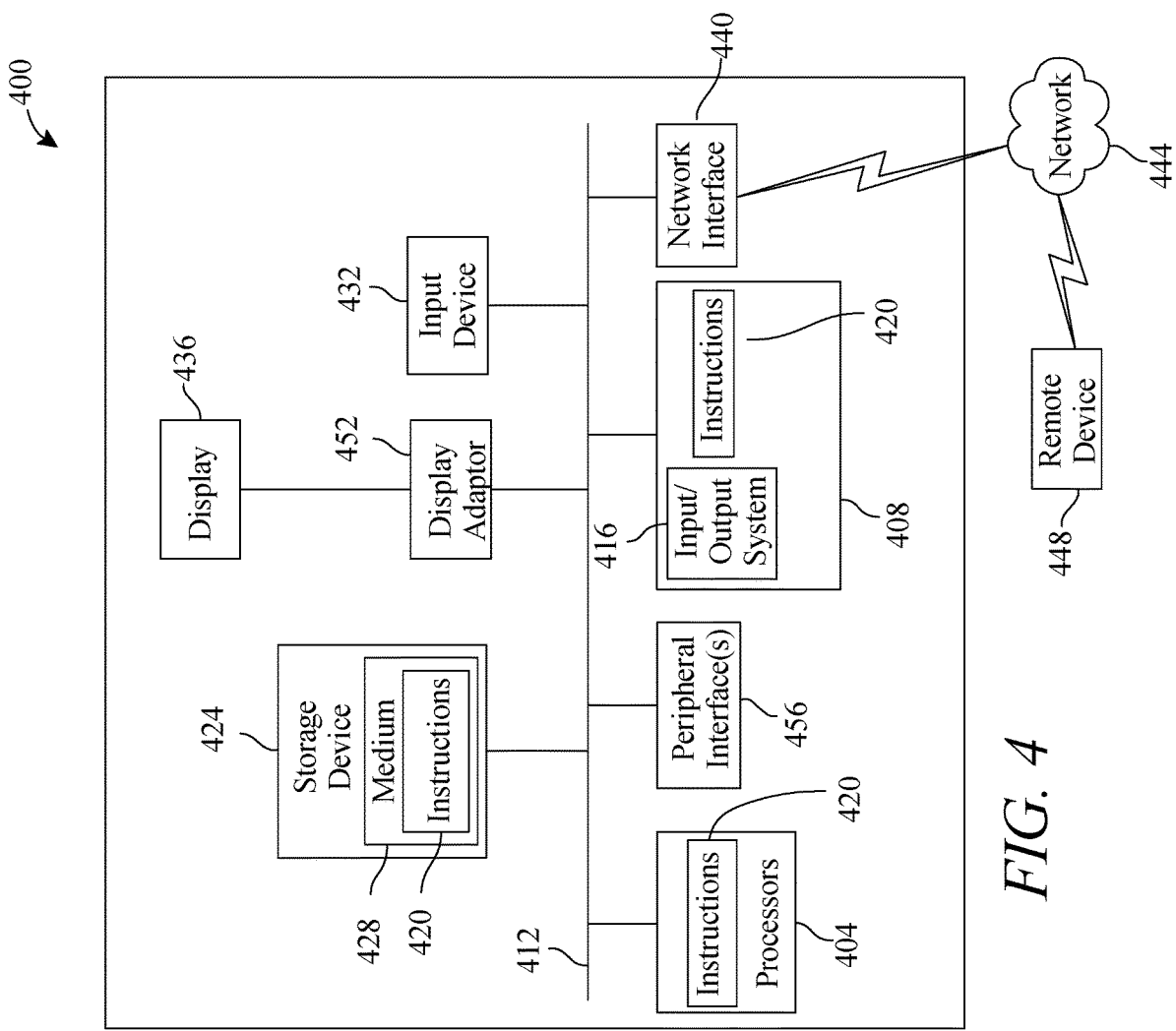
FIG. 4 is a block diagram of a computing system that can be used to implement any one or more of the methodologies disclosed herein and any one or more portions thereof.

FIG. 4 shows a diagrammatic representation of one embodiment of a computing device in the exemplary form of a computer system 400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 400 includes a processor 404 and a memory 408 that communicate with each other, and with other components, via a bus 412. Bus 412 may include any of several types of bus structures including, but not limited to, a memory bus, a memory controller, a peripheral bus, a local bus, and any combinations thereof, using any of a variety of bus architectures.

Processor 404 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 404 may be organized according to Von Neumann and/or Harvard architecture as a non-limiting example. Processor 404 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 408 may include various components (e.g., machine-readable media) including, but not limited to, a random-access memory component, a read only component, and any combinations thereof. In one example, a basic input/output system 416 (BIOS), including basic routines that help to transfer information between elements within computer system 400, such as during start-up, may be stored in memory 408. Memory 408 may also include (e.g., stored on one or more machine-readable media) instructions (e.g., software) 420 embodying any one or more of the aspects and/or methodologies of the present disclosure. In another example, memory 408 may further include any number of program modules including, but not limited to, an operating system, one or more application programs, other program modules, program data, and any combinations thereof.

Computer system 400 may also include a storage device 424. Examples of a storage device (e.g., storage device 424) include, but are not limited to, a hard disk drive, a magnetic disk drive, an optical disc drive in combination with an optical medium, a solid-state memory device, and any combinations thereof. Storage device 424 may be connected to bus 412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 424 (or one or more components thereof) may be removably interfaced with computer system 400 (e.g., via an external port connector (not shown)). Particularly, storage device 424 and an associated machine-readable medium 428 may provide nonvolatile and/or volatile storage of machine-readable instructions, data structures, program modules, and/or other data for computer system 400. In one example, software 420 may reside, completely or partially, within machine-readable medium 428. In another example, software 420 may reside, completely or partially, within processor 404.

Computer system 400 may also include an input device 432. In one example, a user of computer system 400 may enter commands and/or other information into computer system 400 via input device 432. Examples of an input device 432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 432 may be interfaced to bus 412 via any of a variety of interfaces (not shown) including, but not limited to, a serial interface, a parallel interface, a game port, a USB interface, a FIREWIRE interface, a direct interface to bus 412, and any combinations thereof. Input device 432 may include a touch screen interface that may be a part of or separate from display 436, discussed further below. Input device 432 may be utilized as a user selection device for selecting one or more graphical representations in a graphical interface as described above.

A user may also input commands and/or other information to computer system 400 via storage device 424 (e.g., a removable disk drive, a flash drive, etc.) and/or network interface device 440. A network interface device, such as network interface device 440, may be utilized for connecting computer system 400 to one or more of a variety of networks, such as network 444, and one or more remote devices 448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 444, may employ a wired and/or a wireless mode of communication. In general, any network topology may be used. Information (e.g., data, software 420, etc.) may be communicated to and/or from computer system 400 via network interface device 440.

Computer system 400 may further include a video display adapter 452 for communicating a displayable image to a display device, such as display device 436. Examples of a display device include, but are not limited to, a liquid crystal display (LCD), a cathode ray tube (CRT), a plasma display, a light emitting diode (LED) display, and any combinations thereof. Display adapter 452 and display device 436 may be utilized in combination with processor 404 to provide graphical representations of aspects of the present disclosure. In addition to a display device, computer system 400 may include one or more other peripheral output devices including, but not limited to, an audio speaker, a printer, and any combinations thereof. Such peripheral output devices may be connected to bus 412 via a peripheral interface 456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for constitutional analysis using objective functions, the system comprising a computing device, the computing device configured to:
   generate a ranked list of diseases, wherein generating further comprises:
      determining a plurality of disease impact score vectors associated with a plurality of diseases by:
         receiving disease impact training data, the disease impact training data including a plurality of entries correlating diseases of the plurality of diseases with disease impact scores and wherein receiving further comprises generating a user classifier, wherein the user classifier is configured to input user demographic data associated with a user and output disease impact training data;
         training a disease impact model as a function of the disease impact training data and a machine-learning process; and
         determining the plurality of impact score vectors as a function of the disease impact model,
      wherein the plurality of disease impact score vectors includes a disease impact score vector that assesses a degree of susceptibility of improvement;
      generating a first objective function of the impact score vectors; and
      ranking the diseases according to optimization of the first objective function;
   receive, from the user, a plurality of user physiological history data;
   identify, as a function of a disease state classifier, a plurality of disease states associated with the plurality of user physiological history data and, for each disease state, estimate a likelihood that the disease state is present in the user;
   match at least a disease state of the plurality of disease states to the ranked list of diseases; and
   generate a curative habitual pattern to alleviate the at least a disease state, wherein generating further comprises:
      forming a query using the at least a disease state;
      retrieving, from an intervention listing datastore, a plurality of intervention elements as a function of the query;
      combining the plurality of intervention elements to form a plurality of curative habitual pattern candidates;
      calculating a curative impact score of each curative habitual pattern candidate of the plurality of curative habitual pattern candidates by:
         generating a second objective function of the plurality of curative habitual pattern candidates, wherein generating the second objective function further comprises:
            receiving curative training data, the curative training data including a plurality of entries, each entry correlating a curative habitual pattern candidate with at least a curative impact element;
            training a curative machine-learning model as a function of the curative training data and a machine-learning process,
               wherein the curative machine-learning model inputs curative habitual pattern candidates and outputs curative impact vectors; and
            generating the second objective function as an objective function of the curative impact vectors
         optimizing the second objective function; and
      selecting the curative habitual pattern from the plurality of curative habitual pattern candidates as a function of the curative impact score.

2. The system of claim 1, wherein the first objective function further comprises a linear objective function.

3. The system of claim 1, wherein the first objective function further comprises a mixed integer objective function.

4. The system of claim 1, wherein the plurality of user physiological history data includes biological extraction data.

5. The system of claim 1, wherein the computing device is configured to identify the plurality of disease states by determining an age of onset of each disease state of the plurality of disease states.

6. The system of claim 1, wherein a disease state of the user, matched to the ranked list of diseases, is a cardiovascular disease state, and selecting the curative habitual pattern comprises selecting a plan for getting a predetermined minimum number of minutes of cardiovascular exercise per day.

7. The system of claim 1, wherein the computing device is further configured to weight each element of the ranked list, wherein weighting further comprises multiplying a likelihood of a disease state corresponding to an entry in the ranked list by an output of the first objective function for a corresponding disease of the plurality of diseases.

8. The system of claim 1, wherein the computing device is further configured to optimize the first objective function by minimizing a loss function.

9. The system of claim 8, wherein the loss function is minimized by:
   assigning a variable related to a set of parameters, wherein the variables correspond to the disease impact vectors;
   calculating an output of mathematical expression using the variable; and
   selecting a disease impact vector that produces an output having the lowest size.

10. The system of claim 1, wherein the plurality of user physiological history data comprises a self-assessment.

11. A method of constitutional analysis using objective functions, the method comprising:
    generating, by a computing device, a ranked list of diseases, wherein generating further comprises:
       determining a plurality of disease impact score vectors associated with a plurality of diseases by:
          receiving disease impact training data, the disease impact training data including a plurality of entries correlating diseases of the plurality of diseases with disease impact scores and wherein receiving further comprises generating a user classifier, the user classifier configured to input user demographic data associated with a user and output disease impact training data;

training a disease impact model as a function of the disease impact training data and a machine-learning process; and determining the plurality of impact score vectors as a function of the disease impact model, wherein the plurality of disease impact score vectors includes a disease impact score vector that assesses a degree of susceptibility of improvement;

generating a first objective function of the impact score vectors; and ranking the diseases according to optimization of the first objective function;

receiving, by the computing device and from the user, a plurality of user physiological history data;

identifying, by the computing device and as a function of a disease state classifier, a plurality of disease states associated with the plurality of user physiological history data and, for each disease state, estimating a likelihood that the disease state is present in the user;

matching, by the computing device, at least a disease state of the plurality of disease states to the ranked list of diseases; and generating, by the computing device, a curative habitual pattern to alleviate the at least a disease state, wherein generating further comprises:

forming a query using the at least a disease state;

retrieving, from an intervention listing datastore, a plurality of intervention elements as a function of the query;

combining the plurality of intervention elements to form a plurality of curative habitual pattern candidates;

calculating a curative impact score of each curative habitual pattern candidate of the plurality of curative habitual pattern candidates by:

generating a second objective function of the plurality of curative habitual pattern candidates, wherein generating the second objective function further comprises:

receiving curative training data, the curative training data including a plurality of entries, each entry correlating a curative habitual pattern candidate with at least a curative impact element;

training a curative machine-learning model as a function of the curative training data and a machine-learning process, wherein the curative machine-learning model inputs curative habitual pattern candidates and outputs curative impact vectors; and generating the second objective function as an objective function of the curative impact vectors; and optimizing the second objective function; and selecting the curative habitual pattern from the plurality of curative habitual pattern candidates as a function of the curative impact score.

12. The method of claim 11, wherein the first objective function further comprises a linear objective function.

13. The method of claim 11, wherein the first objective function further comprises a mixed integer objective function.

14. The method of claim 11, wherein the plurality of user physiological history data includes biological extraction data.

15. The method of claim 11, wherein identifying the plurality of disease states further comprises determining an age of onset of each disease state of the plurality of disease states.

16. The method of claim 11, wherein selecting the curative habitual pattern comprises selecting a plan for getting a predetermined minimum number of minutes of cardiovascular exercise per day.

17. The method of claim 11, further comprising weighting each element of the ranked list, wherein weighting further comprises multiplying a likelihood of a disease state corresponding to an entry in the ranked list by an output of the first objective function for a corresponding disease of the plurality of diseases.

18. The method of claim 11, further comprising optimize the first objective function by minimizing a loss function.

19. The method of claim 18, further comprising minimizing the loss function by:

assigning a variable related to a set of parameters, wherein the variables correspond to the disease impact vectors;

calculating an output of mathematical expression using the variable; and selecting a disease impact vector that produces an output having the lowest size.

20. The method of claim 11, wherein the plurality of user physiological history data comprises a self-assessment.

* * * * *